United States Patent
Dupelle et al.

(10) Patent No.: US 7,403,807 B2
(45) Date of Patent: Jul. 22, 2008

(54) MEDICAL ELECTRODE WITH PERIPHERAL EDGE OF CONDUCTOR SEALED FROM ELECTROLYTE

(75) Inventors: Michael R. Dupelle, N. Attleboro, MA (US); Sheldon S. White, Brookline, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 104 days.

(21) Appl. No.: 10/900,065

(22) Filed: Jul. 27, 2004

(65) Prior Publication Data

US 2006/0025665 A1 Feb. 2, 2006

(51) Int. Cl.
*A61B 5/04* (2006.01)
*A61N 1/04* (2006.01)

(52) U.S. Cl. .............. 600/372; 600/395; 600/397; 607/152; 607/153

(58) Field of Classification Search ............ 600/372, 600/395, 397; 607/152, 153
See application file for complete search history.

(56) References Cited

U.S. PATENT DOCUMENTS

| | | | |
|---|---|---|---|
| 3,587,565 A * | 6/1971 | Tatoin | 600/391 |
| 4,419,998 A | 12/1983 | Heath | |
| 4,736,752 A * | 4/1988 | Munck et al. | 607/152 |
| 5,356,428 A | 10/1994 | Way | |
| 5,456,710 A * | 10/1995 | Gadsby | 607/142 |
| 5,836,942 A * | 11/1998 | Netherly et al. | 606/32 |
| 6,019,877 A | 2/2000 | Dupelle et al. | |
| 6,356,779 B1 * | 3/2002 | Katzenmaier et al. | 600/391 |
| 6,731,987 B1 * | 5/2004 | McAdams et al. | 607/152 |

* cited by examiner

*Primary Examiner*—Lee S Cohen
(74) *Attorney, Agent, or Firm*—Fish & Richardson P.C.

(57) ABSTRACT

A medical electrode for conducting an electrical current to or from the skin of a patient. The electrode comprises a thin, flexible metallic conductor, a layer of electrolyte in electrical contact with the conductor and positioned to be in electrical contact with the skin when the electrode is applied to a patient, and an insulating layer overlying the conductor, wherein a peripheral edge of the metallic conductor is sealed with an insulating material so that the peripheral edge of the conductor is substantially out of electrical contact with the electrolyte. This tends to increase the shelf life of the electrode because the more highly worked (e.g., from being die cut during manufacture), and thus higher energy state, peripheral edge is electrically isolated.

16 Claims, 2 Drawing Sheets

MEDICAL ELECTRODE WITH PERIPHERAL EDGE OF CONDUCTOR SEALED FROM ELECTROLYTE

TECHNICAL FIELD

This invention relates to medical electrodes, e.g., defibrillation electrodes of the type having a thin metallic conductor and an electrolyte for conducting current between the conductor and the skin.

BACKGROUND

Medical electrodes are applied to the skin for a variety of purposes, including defibrillation, pacing, and monitoring electrical activity (e.g., ECG). A typical medical electrode has a thin metallic conductor (e.g., tin) sandwiched between an insulating backing layer and a conductive gel layer. The metallic conductor is usually cut from sheets of metal by die cutting equipment.

Electrical current flows from the metallic conductor through the gel layer to the skin. The gel layer contains an electrolyte that makes it conductive, and is typically either a nearly solid (highly viscous) gel or a liquid gel supported in a sponge-like layer. Because the gel is normally in contact with the metallic conductor throughout the life of the electrode, corrosion can naturally occur owing to variations in energy levels at the interface between the gel and metallic conductor. This corrosion is often the determining factor in setting the shelf life of the electrode.

One solution proposed for countering corrosion of the metallic conductor is to use stainless steel (U.S. Pat. No. 5,356,428), but, in fact, the corrosion still occurs with stainless steel. U.S. Pat. No. 4,419,998 discloses coating tin with stannous chloride, which helps to reduce corrosion. Putting a rubber layer between the metallic conductor and the gel has been attempted. Replacing the gel with a conductive polymer, to eliminate the salt solution, has been done, but the electrode tends to have poorer connectivity with the skin of the patient, and such conductive polymers tend to be oxygen sensitive and to degrade with age.

Another solution proposed for addressing corrosion, and thereby lengthening the shelf life of such electrodes, is disclosed in U.S. Pat. No. 6,019,877, entitled "Protecting Medical Electrodes from Corrosion", filed on Jun. 18, 1998. A sacrificial element electrically connected to the metallic conductor and also exposed to the gel layer forms an anode-cathode cell in which the sacrificial element functions as a sacrificial anode that corrodes, protecting the metallic conductor, which functions as the cathode, from corrosion.

SUMMARY

We have discovered that a medical electrode can be made more resistant to corrosion, and thus have a longer shelf life, if the periphery of the metallic conductor is sealed from the underlying gel layer so that the periphery is out of electrical contact with the gel. What we have come to appreciate is that in forming the metallic conductor by die cutting, the periphery, where the die cuts the metal, is worked into an effectively higher energy state than other portions of the conductor. The resulting difference in energy state of the metal at the periphery as compared to other locations on the conductor results in an acceleration of the corrosion. By sealing the periphery from the gel, we are able to electrically isolate the metal having this higher energy state.

In general, the invention features a medical electrode for conducting an electrical current to or from the skin of a patient. The electrode comprises a thin, flexible metallic conductor, a layer of electrolyte in electrical contact with the conductor and positioned to be in electrical contact with the skin when the electrode is applied to a patient, and an insulating layer overlying the conductor, wherein a peripheral edge of the metallic conductor is sealed with an insulating material so that the peripheral edge of the conductor is substantially out of electrical contact with the electrolyte.

Preferred implementations of the invention may incorporate one or more of the following: The insulating material sealing the peripheral edge of the metallic conductor may comprise a band covering the peripheral edge of the conductor from a location radially inside the peripheral edge to a location radially outside the peripheral edge. The metallic conductor may be die cut from a sheet of thin, flexible metallic conductor, so that the peripheral edge of the metallic conductor is worked more than the center of the conductor as a consequence of the die cutting, and the area that is worked more is sealed with the insulating material so as to be out of contact with the electrolyte. The band sealing the peripheral edge may extend sufficiently inwardly radially from the peripheral edge as to substantially cover the portion of the conductor that is worked as a consequence of the die cutting. The band may be formed from polyester. The band may be adhered by an adhesive to the peripheral edge of the conductor. The adhesive may be a pressure sensitive adhesive. The pressure sensitive adhesive may be acrylic based. The layer of electrolyte may comprise a solid gel, and the solid gel may be sized and positioned so that its peripheral edge is located radially outward of the radially inner edge of the band, thereby reducing any tendency that the solid gel might have to creep between the band and the metallic conductor. Alternatively, the gel may be sized and positioned so that its peripheral edge is located at approximately the radial location of the radially inner edge of the band. The layer of electrolyte may comprise a solid gel or a liquid gel supported in a sponge layer. The insulating material sealing the peripheral edge of the conductor is a coating applied to the peripheral edge. The coating may be applied by dipping. The coating may be applied by printing. The coating may be applied by bonding under heat and pressure. The coating may be applied by plating with a less active metal than the metal forming the metallic conductor.

Among the many advantages of the invention (some of which may be achieved only in some of its various aspects and implementations) are that electrodes of substantially longer life can be manufactured. And because the corrosive activity initiated by the die cut edges is isolated, it is not as important to use sharp dies in cutting the metallic conductor, as even conductors with relatively ragged cut perimeters can have a long shelf life.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
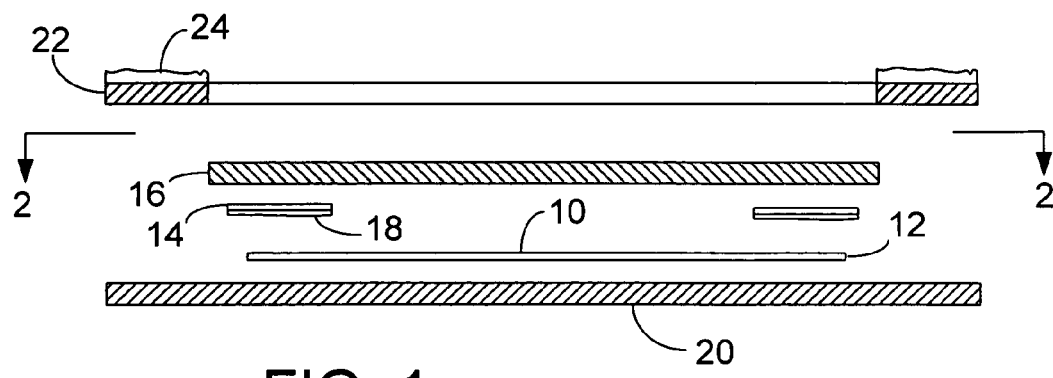
FIG. 1 is an exploded, diagrammatic, cross-sectional view of one implementation of the invention, taken at section 1-1 in FIG. 2.
Figure 2:
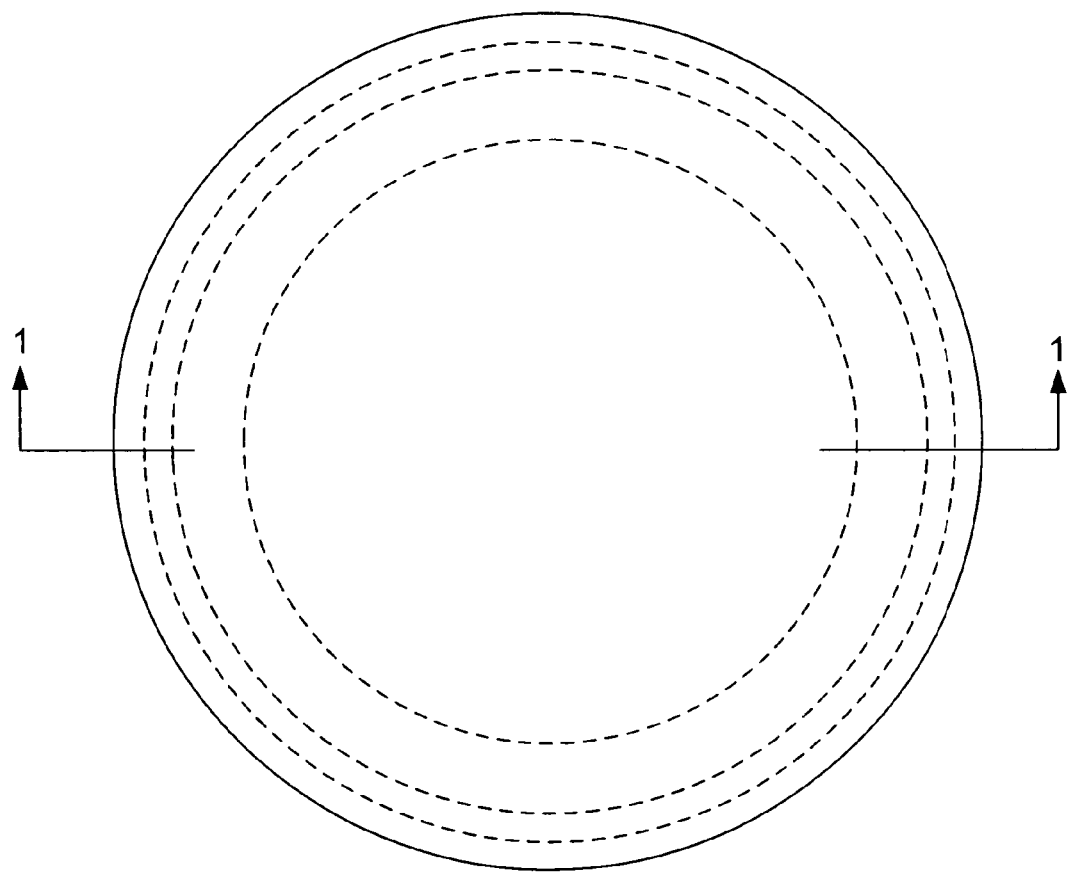
FIG. 2 is a partial plan view taken at 2-2 of FIG. 1.

The descriptions below are more than sufficient for one skilled in the art to construct the disclosed implementations. Unless otherwise mentioned, the processes and manufacturing methods referred to are ones known by those working in the art FIGS. 1 and 2 show one implementation of the invention. A flexible metallic conductor 10 (e.g., 0.0005 to 0.005 in. thick; tin, aluminum or salt of a metal) has its peripheral edge 12 sealed with a polyester band 14 (e.g., 1 mil thick Mylarâ) positioned so that the band extends from a location radially inside the peripheral edge to a position radially outside the edge. Various types of adhesive 18 can be used to adhere the band to the metallic conductor (e.g., an acrylic-based pressure sensitive adhesive such as Lohmann Therapy Systems P/N MTC611; or a rubber-based pressure sensitive adhesive; or a silicone sealant). The adhesive should preferably be one that will continue to function for longer than the expected shelf life of the electrode, and is preferably a material that will not be attacked during the life of the electrode.

Figure 3:
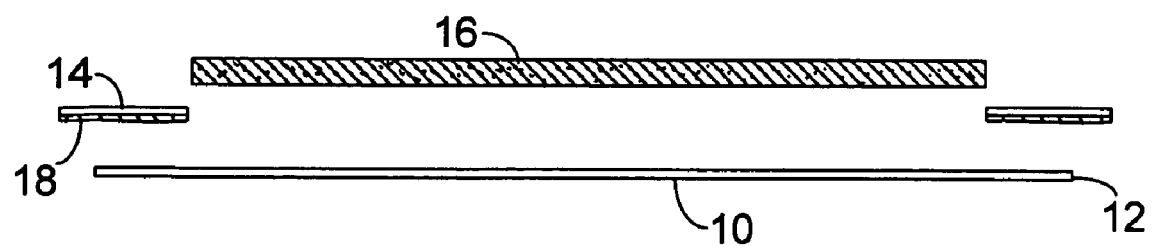
FIG. 3 is an exploded, partial, diagrammatic, cross-sectional view of a second implementation.

Gel layer 16 can be either solid gel (e.g., 0.020 to 0.030 in. thick hydrogel) or a liquid gel supported by a sponge layer (e.g., 0.125 to 0.250 in. thick). The gel layer may be cut so that its perimeter extends radially outside the inner edge of the band. In the figures, the gel layer extends radially outside of the outer edge of the band, also. There may be an advantage to having the gel layer overlap the band as shown here, as it tends to lessen the likelihood that the gel will creep into the seal between the band the metallic conductor. But it may be possible to cut the gel material as shown in FIG. 3 so that it fits inside the band, with its outer perimeter butting against the inside perimeter of the band. A concern with this construction may be that the gel will tend to creep into the adhesive seal 18 between the band and the metallic conductor, but whether, and how rapidly, that occurs will vary with materials, and so that construction may work quite well.

An insulating backing layer 20 overlies the metallic conductor 10, and a skin-adhering layer 22, with adhesive 24, is used to adhere the electrode to the skin (FIG. 1). For simplicity, layers 20, 22, and 24 are not shown in the implementation of FIG. 3, but they would typically be present.

Figure 4:
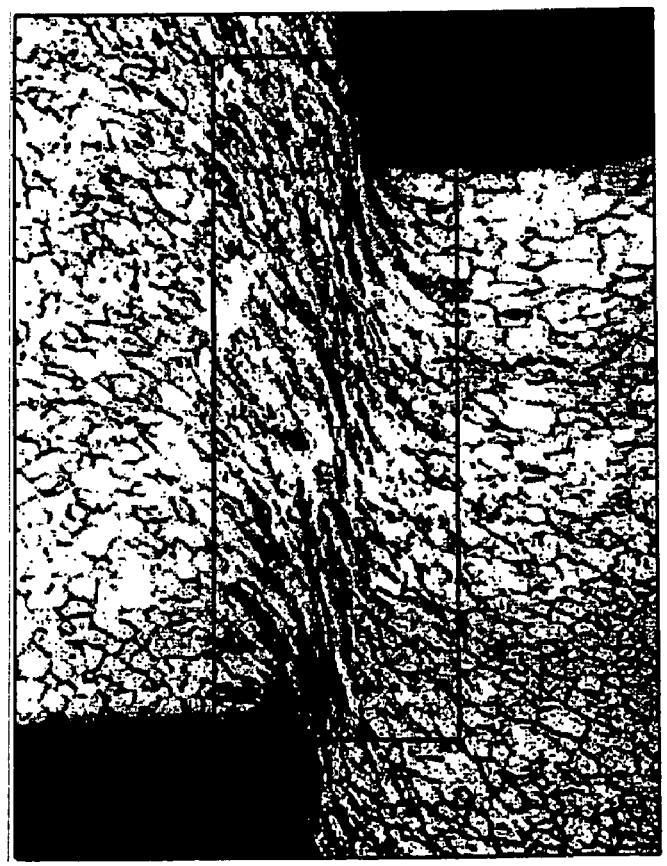
FIG. 4 is a photograph illustrating working of a metallic conductor.

FIG. 4 is a photograph of the structure of a metallic conductor illustrating the working of a metallic conductor that can occur as a result of cutting the peripheral edge. In the photograph, the conductor has not been cut through, but has been sheared by the action of mating dies so as to clearly show the metallurgical differences between the severely cold worked portions that will become the sheared material edges and the initial much lesser worked structure. The severely cold worked portions are seen in the center of the photograph. With continued shearing action, the center will be split in two, with the severely cold worked portions becoming the sheet edges. These edges, being so much more cold worked than the initial structure, will behave like anodes if in electrical contact with the electrolyte, i.e., they will preferentially corrode, because the worked areas are so much higher in energy.

Cold working that occurs at the edges results in significant displacement of the metallic atoms from their equilibrium positions. The atoms in these severely cold worked regions are forced closer to or further away from each other than normal, with the result that the atoms have a higher energy level than is associated with atoms at normal spacing from their neighbors. The higher energy level means that the affected atoms have a higher propensity to react faster and more vigorously than atoms in regions having a lesser amount of cold work. The net result is that severely cold worked metal is more reactive than metal of exactly the same chemical composition having lesser amount of cold work, and thus, in the presence of a corrosive medium, the severely cold worked portions of a single piece of metal will corrode preferentially to portions having lesser amounts of cold work.

The corrosion brought on by severe cold working not only reduces the amount of metal available for electrical conduction, but also promotes the formation of corrosion byproducts, which tend to have poor conductivity and to further inhibit the flow of electricity through the metal conductor (and, hence, through the electrode). And chemical interactions between the cut edges and the gel may reduce the amount (and composition) of chemically active gel needed for the function of the electrode. Also, the chemical interactions between the cut edges and the gel may affect the chemical tackiness of the gel, thereby reducing the effectiveness of the adhesive bond between the gel and the skin.

Many other implementations of the invention other than those described above are within the invention, which is defined by the following claims. For example, instead of bonding a band to the peripheral edge of the metallic conductor, the edge may be sealed by printing or by dipping, in which case the insulating material would typically cover both the top and bottom surfaces of the periphery. Also, the band may be bonded to the periphery using heat and pressure, without the use of a separate adhesive layer. The edge could be sealed by plating it with a less active (more noble) metal than the metal used for the flexible conductor. The gel layer could be any of various types, e.g. a solid gel or a liquid gel supported in a sponge layer.

What is claimed is:

1. A medical electrode for conducting an electrical current to or from the skin of a patient, the electrode comprising:
    a flexible metallic conductor, the conductor having a peripheral edge,
        wherein the peripheral edge of the metallic conductor has at least some regions that have been worked more during manufacturing than other regions of the metallic conductor;
    a layer of electrolyte in electrical contact with the conductor and positioned to be in electrical contact with the skin when the electrode is applied to a patient, the layer of electrolyte having a peripheral area that overlaps the peripheral edge of the conductor, an insulating layer overlying the conductor,
    wherein a peripheral edge of the metallic conductor is sealed with an insulating material so that the regions that have been worked more are substantially out of electrical contact with the overlapping peripheral area of the layer of electrolyte,
    wherein the insulating material and the seal of the insulating material to the peripheral edge of the conductor is configured to reduce corrosion of the conductor at the regions of the peripheral edge that have been worked more.

2. The medical electrode of claim 1 wherein the flexible metallic conductor is die cut from a sheet of thin, flexible metallic conductor, so that the peripheral edge of the metallic conductor has the regions that have been worked more as a consequence of the die cutting.

3. The medical electrode of claim 1 wherein the insulating material sealing the peripheral edge of the metallic conductor comprises a band covering the peripheral edge of the conductor from a location radially inside the peripheral edge to a location radially outside the peripheral edge.

4. The medical electrode of claim 2 wherein the insulating material sealing the peripheral edge of the metallic conductor comprises a band covering the peripheral edge of the conductor from a location radially inside the peripheral edge to a location radially outside the peripheral edge, and wherein the band extends sufficiently inwardly radially from the peripheral edge of the conductor as to substantially cover the portion of the conductor that is worked as a consequence of the die cutting.

5. The medical electrode of claim 3 or 4 wherein the band is formed from polyester.

6. The medical electrode of claim 3 or 4 wherein at least a portion of the band is adhered by an adhesive to the peripheral edge of the conductor.

7. The medical electrode of claim 6 wherein the adhesive is a pressure sensitive adhesive.

8. The medical electrode of claim 7 wherein the pressure sensitive adhesive is acrylic based.

9. The medical electrode of claim 6 wherein the layer of electrolyte comprises a solid gel, and wherein the solid gel is sized and positioned so that its peripheral edge is located radially outward of the radially inner edge of the band, thereby reducing any tendency that the solid gel might have to creep between the band and the metallic conductor.

10. The medical electrode of claim 6 wherein the layer of electrolyte comprises a solid gel, and wherein the solid gel is sized and positioned so that its peripheral edge is located at approximately the radial location of the radially inner edge of the band.

11. The medical electrode of claim 1 or 2 wherein the layer of electrolyte comprises a liquid gel supported in a sponge layer.

12. The medical electrode of claim 1 or 2 wherein the insulating material sealing the peripheral edge of the conductor is a coating applied to the peripheral edge.

13. The medical electrode of claim 12 wherein the coating is applied by dipping.

14. The medical electrode of claim 12 wherein the coating is applied by printing.

15. The medical electrode of claim 12 wherein the coating is applied by bonding under heat and pressure.

16. The medical electrode of claim 12 wherein the coating is applied by plating with a less active metal than the metal forming the metallic conductor.

* * * * *